United States Patent [19]
Ockuly et al.

[11] Patent Number: 5,868,733
[45] Date of Patent: Feb. 9, 1999

[54] GUIDING INTRODUCER SYSTEM FOR USE IN THE TREATMENT OF ACCESSORY PATHWAYS AROUND THE MITRAL VALVE USING A RETROGRADE APPROACH

[75] Inventors: John D. Ockuly, Minnetonka; James A. Hassett, Bloomington, both of Minn.

[73] Assignee: Daig Corporation, Minnetonka, Minn.

[21] Appl. No.: 421,901

[22] Filed: Apr. 14, 1995

Related U.S. Application Data

[63] Continuation-in-part of Ser. No. 388,800, Feb. 14, 1995, Pat. No. 5,640,955.

[51] Int. Cl.$^6$ .......................... A61B 17/36; A61M 37/00
[52] U.S. Cl. .......................... 606/10; 604/281; 604/164
[58] Field of Search ................... 606/10, 11, 12, 606/15, 16, 17; 604/164, 280, 281, 20

[56] References Cited

U.S. PATENT DOCUMENTS

| | | | |
|---|---|---|---|
| 4,581,017 | 4/1986 | Sahota . | |
| 4,810,244 | 3/1989 | Allen | 604/44 |
| 4,935,017 | 6/1990 | Sylvanowicz | 604/280 |
| 5,078,684 | 1/1992 | Yasuda | 604/95 |
| 5,120,323 | 6/1992 | Shockey et al. . | |
| 5,267,982 | 12/1993 | Sylvanowicz . | |
| 5,279,546 | 1/1994 | Mische et al. | 604/22 |
| 5,290,229 | 3/1994 | Paskar | 604/95 |
| 5,304,131 | 4/1994 | Paskar | 604/95 |
| 5,324,284 | 6/1994 | Imran | 606/15 |
| 5,330,466 | 7/1994 | Imran | 606/15 |
| 5,370,109 | 12/1994 | Cuny | 604/281 |
| 5,464,404 | 11/1995 | Abela et al. | 606/15 |
| 5,575,766 | 11/1996 | Swartz et al. | 604/53 |
| 5,628,316 | 5/1997 | Swartz et al. | 128/657 |
| 5,656,028 | 8/1997 | Swartz et al. | 604/53 |

*Primary Examiner*—Jennifer Bahr
*Assistant Examiner*—Sonya Harris-Ogura
*Attorney, Agent, or Firm*—Scott R. Cox

[57] ABSTRACT

A process for the mapping and/or ablating of accessory pathways around the mitral valve using a retrograde approach by use of ablating and/or mapping catheters guided by a guiding introducer system. Also disclosed are shapes for an inner and outer guiding introducers which comprise the guiding introducer system.

28 Claims, 4 Drawing Sheets

GUIDING INTRODUCER SYSTEM FOR USE IN THE TREATMENT OF ACCESSORY PATHWAYS AROUND THE MITRAL VALVE USING A RETROGRADE APPROACH (b) This application is a continuation-in-part of application Ser. No. 08/388,800, filed Feb. 14, 1995 now U.S. Pat. No. 5,640,955.

(c) BACKGROUND OF THE INVENTION

1. Field of Invention

This invention relates to introducers. More particularly, this invention relates to a guiding introducer system for use within the left ventricle of the human heart for the treatment of accessory pathways around the mitral valve.

2. Prior Art

Introducers and catheters have been in use for medical procedures for many years. For example, one use has been to convey an electrical stimulus to a selected location within the human body. Another use is to monitor and make measurements for diagnostic tests within the human body. Catheters may be used by a physician to examine, diagnose and treat while positioned at a specific location within the body which is otherwise inaccessible without more invasive procedures. In use, catheters may be inserted into a major vein or artery which is near the body surface. These catheters are then guided to the specific location for examination, diagnosis or treatment by manipulating the catheter through the artery or vein of the human body.

Catheters have become increasingly useful in remote and difficult to reach locations within the body. However, the utilization of these catheters is frequently limited because of the need for the precise placement of the tip of the catheter at a specific location within the body.

Control of the movement of catheters to achieve such precise placement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, through various arteries or veins until the tip of the catheter reaches the desired location in the heart.

The distal end of a catheter used in such a procedure is sometimes preformed into a desired curvature so that by torquing the catheter about its longitudinal axis, the catheter can be manipulated to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 5,231,994 discloses a guide catheter for guiding a balloon catheter for the dilation of coronary arteries. U.S. Pat. No. 4,117,836 discloses a catheter for the selective coronary angiography of the left coronary artery and U.S. Pat. Nos. 5,215,540, 5,016,640 and 4,883,058 disclose catheters for selective coronary angiography of the right coronary artery. U.S. Pat. No. 5,242,441 discloses a deflectable catheter for ablation procedures in the ventricular chamber. See also U.S. Pat. No. 4,033,331. In addition, U.S. Pat. No. 4,898,591 discloses a catheter with inner and outer layers containing braided portions. The '591 patent also discloses a number of different curvatures for intravascular catheters. Thus, there are a number of references which disclose catheters with predetermined shapes, designed for use during specific medical procedures generally associated with the heart or the vascular system. Because of precise physiology of the heart and the vascular system, catheters or introducers with precisely designed shapes for predetermined uses within the human heart and vascular system are increasingly important.

In addition to single catheters with various curvatures, U.S. Pat. No. 4,581,017 discloses an inner and outer guide catheter, (numbers 138 and 132), for use with a balloon catheter for treatment of coronary arteries. U.S. Pat. No. 5,267,982 discloses a catheter assembly and methods for catheterization of coronary arteries wherein an inner catheter (50) and outer catheter (52) are used in combination for the treatment of right and left coronary angiographic procedures. See also U.S. Pat. No. 4,935,017 which discloses a similar device. U.S. Pat. No. 5,290,229 discloses a straight outer sheath and a preformed inner catheter for use in the heart. See also U.S. Pat. Nos. 5,304,131, 5,120,323, 4,810, 244 and 5,279,546.

Catheter ablation of accessory pathways using a long vascular sheath by means of a transseptal or retrograde approach is discussed in Saul, J. P., et al. "Catheter Ablation of Accessory Atrioventricular Pathways in Young Patients: Use of long vascular sheaths, the transseptal approach and a retrograde left posterior parallel approach" *J. Amer. Coll. Card.*, Vol. 21, no. 3, pps 571–583 (Mar. 1, 1993). See also Swartz, J. F. "Radiofrequency Endocardial Catheter Ablation of Accessory Atrioventricular Pathway Atrial Insertion Sites" *Circulation*, Vol. 87, no. 2, pps. 487–499 (February, 1993).

U.S. Pat. No. 4,641,649 discloses the use of high frequency energy for the treatment of tachycardia or cardiac dysrhythmia. See also U.S. Pat. No. 4,945,912 for the use of radio frequency energy for ablation of cardiac tissue. In addition, various articles have disclosed the ablation of specific locations within the heart by use of energy, in particular, radio frequency energy. See, for example, Gallagher, J. J. et al. "Catheter Technique for Closed-Chest Ablation of the Atrioventricular Conduction System" N. Engl. J. Med. Vol. 306, pp. 194–200 (1982); Horowitz, L. N. "Current Management of Arrhythmia" pp. 373–378 (1991); Falk, R. H. et al. "Atrial Fibrillation Mechanics and Management" pp. 359–374 (1992); and Singer, I. "Clinical Manual of Electrophysiology" pp. 421–431 (1993).

In addition, the use of radio frequency ablation energy for the treatment of Wolff-Parkinson-White Syndrome in the left atrium by use of a transseptal sheath is disclosed in Swartz, J. F. et al. "Radiofrequency Endocardial Catheter Ablation of Accessory Atrioventricular Pathway Atrial Insertion Sites" Circulation Vol. 87, pp. 487–499 (1993). See also Tracey, C. N. "Radio Frequency Catheter Ablation of Ectopic Atrial Tachycardia Using Paced Activation Sequence Mapping" J. Am. Coll. Cardiol. Vol. 21, pp. 910–917 (1993). See also U.S. Pat. Nos. 5,172,699, 5,222,501 and 5,242,441.

Accordingly, it is an object of this invention to prepare a guiding introducer system for selected medical procedures in the left ventricle.

It is a further object of this invention to prepare a guiding introducer system for use in selected electrophysiology procedures within the left ventricle of the heart.

Another object of this invention is to prepare a guiding introducer system for use in selected ablation procedures within the left ventricle of the heart.

These and other objects are obtained by the design of the guiding introducer system disclosed in the instant invention.

(d) SUMMARY OF THE INVENTION

The instant invention includes a process for the ablation and mapping of accessory pathways around the mitral valve of the left ventricle of the heart using a retrograde approach comprising (a) introducing into the left ventricle a guiding introducer system, wherein said guiding introducer system is comprised of an inner and outer guiding introducer, wherein each of the inner and outer guiding introducers contains a lumen running lengthwise therethrough, a proximal and a distal end;

(b) introducing the inner guiding introducer into the lumen of the outer guiding introducer;

(c) introducing into the lumen of the inner guiding introducer an ablation or mapping catheter containing a proximal and distal end, wherein said catheter has one or more electrodes located at or near the distal end of the catheter;

(d) guiding the catheter to a selected location about the mitral valve of the heart on the ventricular side by use of the guiding introducer system; and (e) mapping or ablating the selected location about the mitral valve by use of the electrodes of the catheter.

In addition, the instant invention is a guiding introducer system to be used for mapping and/or ablating locations about the mitral valve from the ventricular side comprising an inner and an outer guiding introducer.

(f) DETAILED DESCRIPTION OF THE DRAWINGS

A typical human heart includes a right ventricle, a right atrium, left ventricle and left atrium. The right atrium is in fluid communication with the superior vena cava and the inferior vena cava. The atrioventricular septum 10 separates the atria from the ventricles. The tricuspid valve 12 contained within the atrioventricular septum communicates the right atrium with the right ventricle. The mitral valve 14 contained within the atrioventricular septum communicates the left atrium with the left ventricle. See FIG. 1A. On the inner wall of the right atrium, where it is connected with the left atrium, is a recessed portion, the fossa ovalis. Between the fossa ovalis and the tricuspid valve 12 is the opening or ostium for the coronary sinus. The coronary sinus is the large epicardial vein which accommodates most of the venous blood which drains from the myocardium into the right atrium.

Figure 1A:
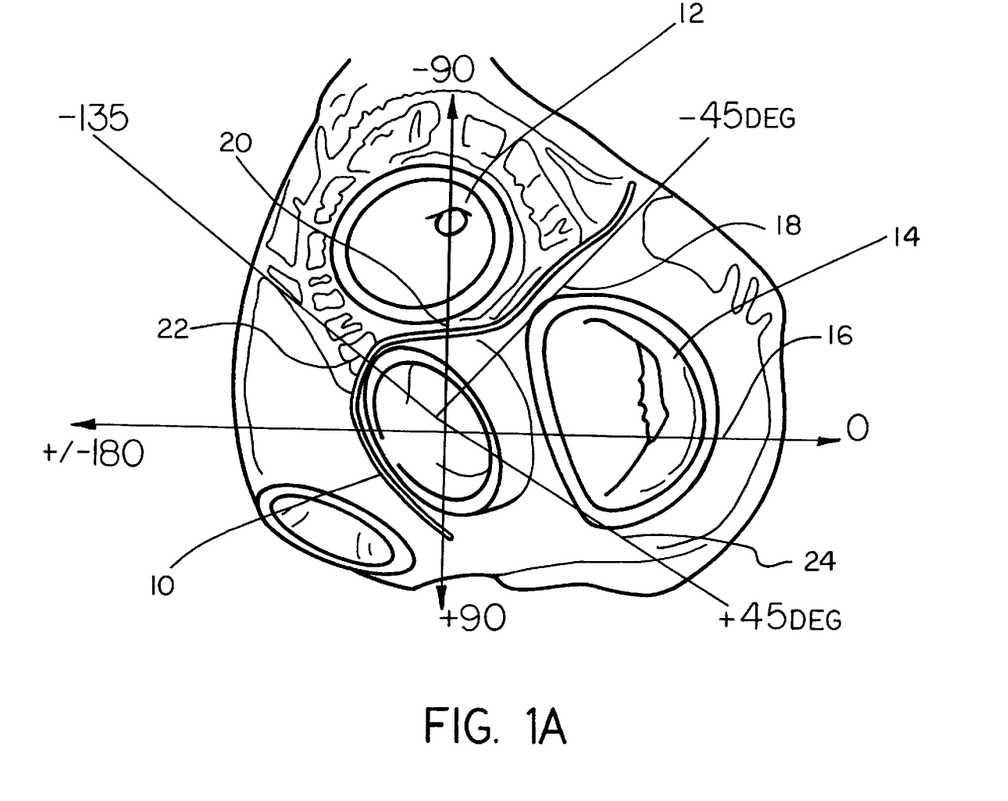
FIG. 1A is a cross-section from above the heart of a portion of the left side of the heart showing the mitral valve, aortic valve, tricuspid valve and pulmonary valve defining the position of those features of the heart relative to the aortic valve.

In the normal heart, contraction and relaxation of the heart muscle (myocardium) takes place in an organized fashion as electro-chemical signals pass sequentially through the myocardium from the atrial to the ventricular tissue along a well defined route which includes the His-Purkinje system. Initial electric impulses are generated at the sinuatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve 12 through the atrioventricular septum 10 and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, patients diagnosed with Wolff-Parkinson-White syndrome (W-P-W) have an arrhythmia. The cause of this arrhythmia is the existence of an anomalous conduction pathway or pathways that connect the atria muscle tissue directly to the ventricular muscle tissue, thus by-passing the normal His-Purkinje system. These pathways are usually located in the fibrous tissue that connect the atrium and the ventricle. In recent years a technique has been developed to destroy these anomalous conduction pathways by delivering energy into the tissue in which the pathways exist. To accomplish this procedure a special catheter 50 with ablation electrodes is positioned as close as possible to the anomalous conduction pathway to maintain constant tissue contact while energy is delivered to destroy the pathway. This same type of contact with the cardiac tissue is also necessary when mapping or other procedures are employed relating to these pathways.

Figure 1B:
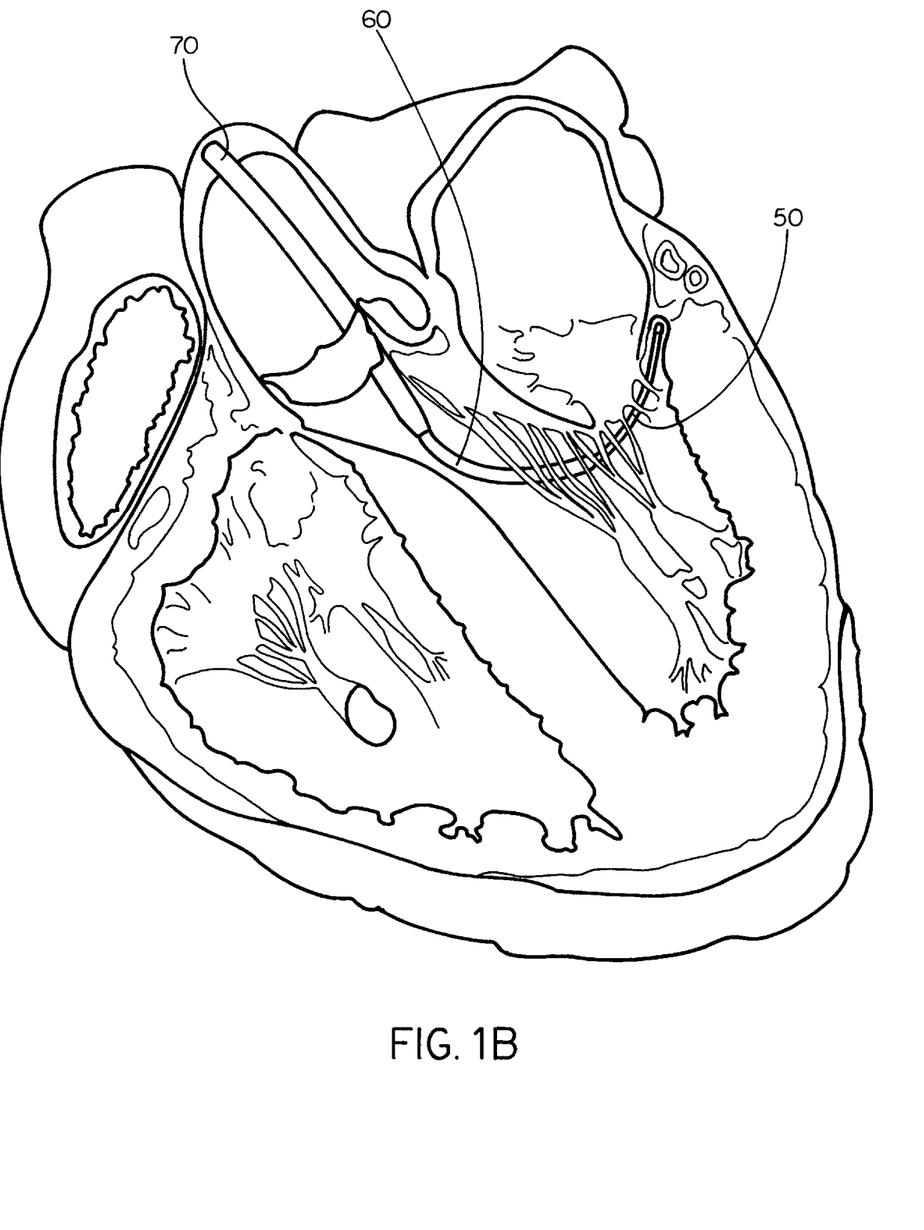
FIG. 1B is a cut-away view of a portion of the left side of the heart showing the guiding introducer system for supporting a catheter to ablate a left lateral accessory pathway.

One end of these anomalous conduction pathways can be located either in the right atrium or in the left atrium with the other end of the pathway located in the corresponding ventricle. When the anomalous conduction pathway is located between the left atrium and the left ventricle, there are two approaches to positioning the catheter 50 near that pathway for the appropriate medical procedure. One is to introduce the catheter 50 into the femoral artery by an introducer and advance it up the aorta, across the aortic valve into the left ventricle and then position its tip under the mitral valve annulus near the anomalous conduction pathway. See FIGS. 1A and 1B. This is commonly referred to as the "retrograde" approach.

The other approach, commonly referred to as the transseptal approach, is to introduce a transseptal sheath apparatus, into the right femoral vein and advance it through the inferior vena cava into the right atrium. A puncture is then made through the fossa ovalis in the interatrial septum and the apparatus is advanced into the left atrium where the trocar and dilator of the apparatus are removed, leaving the sheath in position in the left atrium. The mapping or ablation catheter 50 is then inserted through the sheath and into the left atrium and positioned on top of the mitral valve annulus near the anomalous conduction pathway. Specific positions may be chosen for the mapping or ablation on the left side of the heart, including specifically postero lateral, lateral 16, antero lateral, posterior 18, postero septal 20, septal 22, antero medial and anterior 24 positions around the mitral valve annulus. See FIG. 1A.

Mere introduction of the ablation and mapping catheter 50 into the left ventricle for a retrograde approach is not sufficient to effectively and efficiently perform these medical procedures, especially for the mapping or ablation of anomalous conduction pathways. The medical practitioner commonly monitors the introduction of the catheter and its progress through the vascular system by a fluoroscope. Such fluoroscopes cannot easily identify the specific features of the heart in general, and the critically important structures of the left ventricle in specific, thus making placement of the ablation electrode of the ablation catheter difficult. This placement is especially difficult as the beating heart is in motion. In addition, the ablation catheter 50 will be moving within the left ventricle as blood is being pumped through the heart throughout the procedure. Further, because of the difficulty of properly locating the catheter 50, extended exposure to fluoroscopy is undesirable, but sometimes inevitable.

The guiding introducer system of the instant invention address and solve these problems. Referring now to FIGS. 2A, 2B, 3A and 3B, the guiding introducer system of the present invention for use in the left ventricle is comprised of an inner 60 and an outer guiding introducer. The inner guiding introducer 60 is preferably longer than the outer guiding introducer 70 so that its distal end may be extended out from the distal end of the outer guiding introducer 70 to form various curves and shapes. In use, the inner guiding introducer 60 is inserted into the outer guiding introducer 70 until the distal end of the inner guiding introducer 60 extends out from the distal end of the outer guiding introducer 70. The inner 60 and outer guiding introducer are generally each comprised of two sections. (Each section is preferably formed as an integral portion of the entire guiding introducer without discrete sections. However, the division of each of the guiding introducers into two different sections for discussion better defines the overall shape of the guiding introducers.) The inner 60 and outer 70 guiding introducers will be shown in two views. In each of the views for ease of analysis, the inner 60 and outer 70 guiding introducer will be secured to a valve for attachment to a conventional side port tubing and stop cock 68, 78. In each such arrangement, the shape of the inner 60 and outer 70 guiding introducer will be described, making reference to its position in relation to the side port and side port tubing 68, 78 where the proximal end of the inner 60 and outer 70 guiding introducer is secured to the side port tubing 68, 78. In the first referenced figure (FIGS. 2A and 3A), the side port tubing 68, 78 is generally viewed as if it is behind the first section of the inner 60 or outer 70 guiding introducer. The remaining figures (FIGS. 2B and 3B) will show the inner 60 and outer 70 guiding catheter after clockwise rotation about the axis of the first section of the inner 60 and outer 70 guiding introducer when viewed from the perspective of the proximal end of the respective guiding introducer.

Figure 2A:
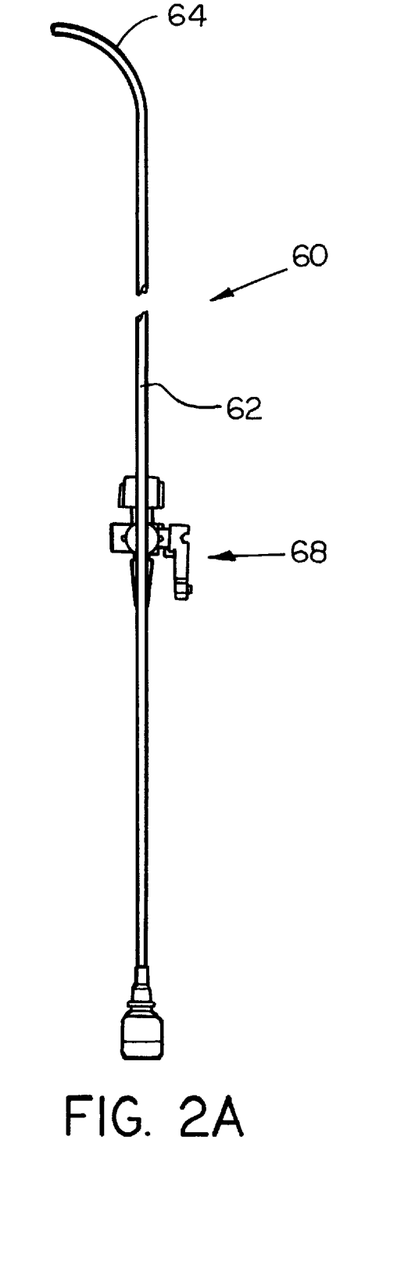
FIG. 2A is a side view of the inner guiding introducer for use in the left ventricle around the mitral valve, wherein the side port tubing attached to the proximal end of the inner guiding introducer is located directly behind the first section of the guiding introducer.
Figure 2B:
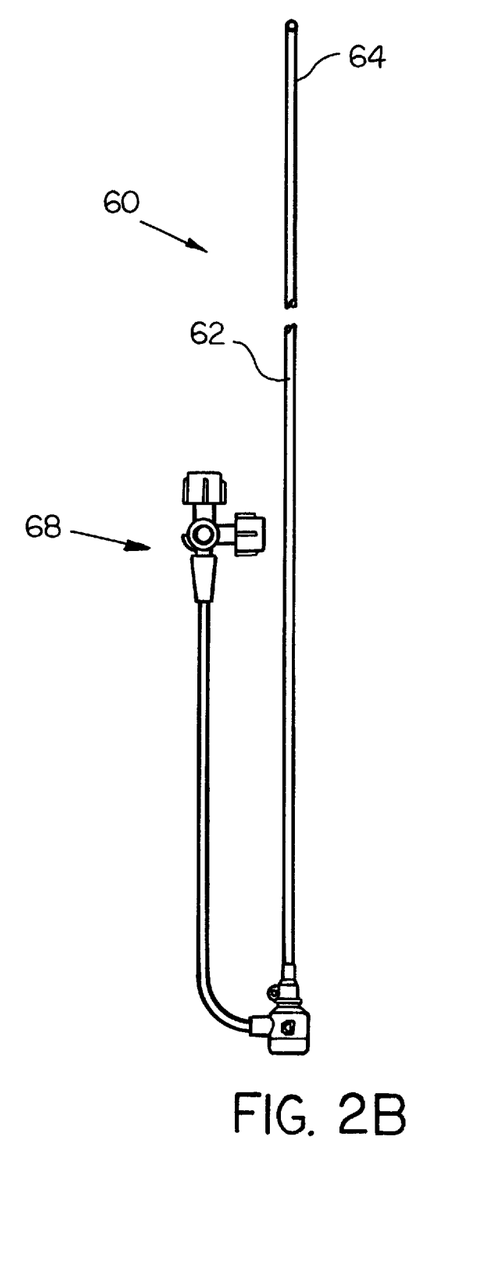
FIG. 2B is a side view of the inner guiding introducer rotated 90 degrees clockwise from the position of FIG. 2A, when viewed from the perspective of the proximal end of the inner guiding introducer, such that the side port tubing is directed to the left of the guiding introducer.

The first section 62 of the inner guiding introducer 60 is a conventional, elongated, hollow, generally straight section of sufficient length for introduction into the patient and for manipulation from the point of insertion to the specific desired location within the heart. (The overall length of the first section 62 as shown in the figures has been reduced for ease of viewing.)

Merged with the distal end of the first section 62 of the inner guiding introducer 60 is the second section which is a smooth, generally flat curve, curving to the left as shown in FIG. 2A. This curve has a radius of from about 0.5 in. to about 1.5 in. and preferably from about 0.7 in. to about 1.3 in. The extent of the arc of the curve is from about 45 to about 135 degrees and preferably from about 60 to about 120 degrees of arc, ending in the distal tip of the inner guiding introducer 60. While the curve is preferably a single, smooth curve, alternatively two or more separate curved sections, each with the same or different curvature and radii, alone or in combination with one or more short straight sections, can be used in combination to form the overall curve as long as the overall curvature is approximately the same as above described. The first and second sections are preferably coplanar (within about 15 degrees of coplanar.)

The outer guiding introducer 70 (FIGS. 3A and 3B) is designed for use with the inner guiding introducer 60 for ablation procedures relating to the left ventricle of the heart. The first section 72 of the outer guiding introducer 70 is a conventional, elongated, hollow, generally straight section of sufficient length for introduction into the patient and for manipulation from the point of insertion to the specific desired location within the heart. (The overall length of the first section as shown in the figures has been reduced for ease of viewing.)

Figure 3A:
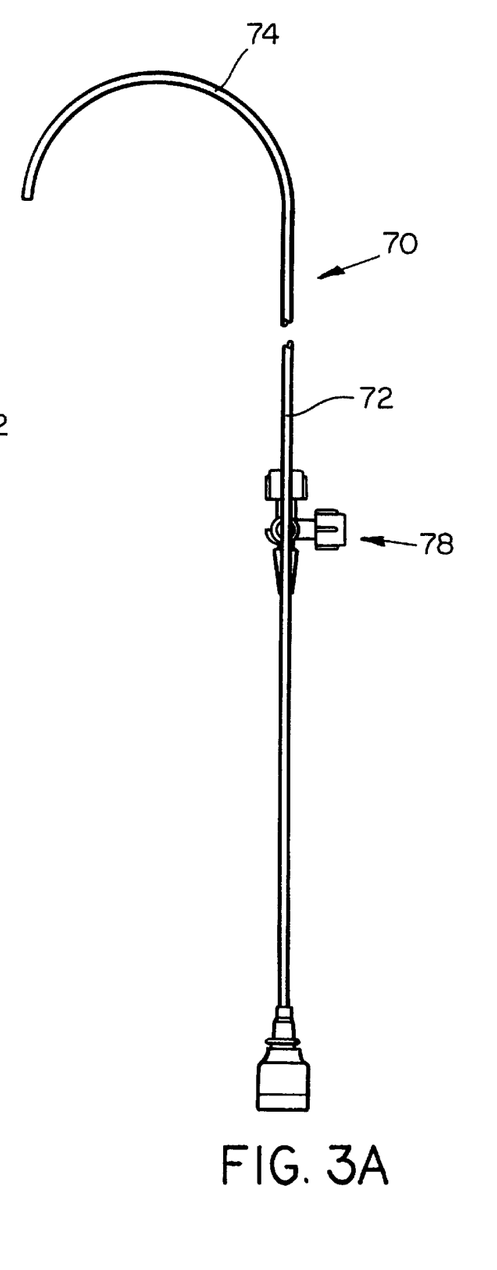
FIG. 3A is a side view of the outer guiding introducer for use in the left ventricle around the mitral valve, wherein the side port tubing attached to the proximal end of the outer guiding introducer is located directly behind the first section of the outer guiding introducer.
Figure 3B:
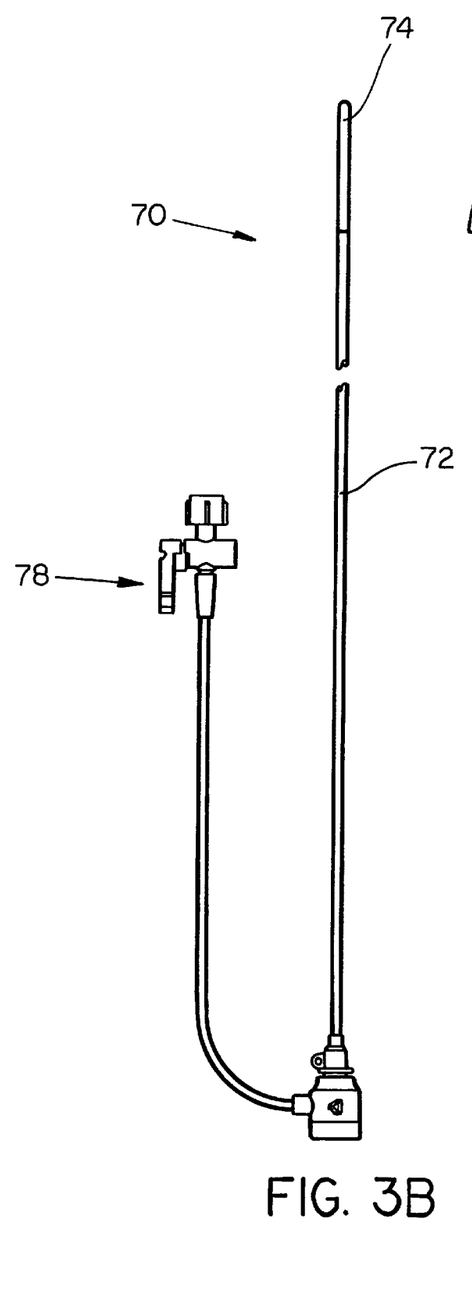
FIG. 3B is a side view of the outer guiding introducer rotated 90 degrees clockwise from the position of FIG. 3A, when viewed from the perspective of the proximal end of the outer guiding introducer, such that the side port tubing is directed to the left of the outer guiding introducer.

Merged with the distal end of the first section 72 of the outer guiding introducer is the second section which is a smooth, generally flat curve curving to the left as shown in FIG. 3A. This curve has a radius of from about 1.0 to about 2.0 in. and preferably from about 1.3 to about 1.7 in. The extent of the arc of the curve is from about 135 to about 225 degrees, and preferably from about 150 to about 210 degrees of arc, ending in the distal tip of the outer guiding introducer. As with the inner guiding introducer 60, the second section 74 may be comprised of a single continuously curving curved section or it can be a combination of separate curved and alternatively, straight sections to form the overall curve as long as the overall arc of the curve is generally the same as is above described.

The distal tip of the inner 60 and outer 70 guiding introducers may be, and preferably will be, tapered to form a good transition with a dilator. This tapering is preferably less than 10° and more preferably about 4° to about 7°. The inner 60 and outer 70 guiding introducers preferably may also contain one or a multitude of radiopaque tip marker bands near the distal tip of the inner and outer guiding introducer. The inner 60 and outer 70 guiding introducer also preferably contain one or a plurality of vents near the distal tip of the inner 60 and outer 70 guiding introducer, preferably three or four such vents. The vents are preferably located no more than about 1.00 in. from the tip of the inner 60 and outer 70 guiding introducer and more preferably 0.10 to about 1.00 in. from the tip. The size of these vents should be in the range of about 40 to about $^{60}/_{1000}$ of an inch in diameter. These vents are designed to prevent air from entering the inner 60 and outer 70 guiding introducer caused by the withdrawal of the catheter contained within the inner 60 and outer 70 guiding introducer in the event the distal end of the inner 60 and outer 70 guiding introducer is occluded. For example, if the tip of one of the guiding introducers is placed against the myocardium and the catheter located within the inner guiding introducer is withdrawn, a vacuum may be created within the guiding introducer system if no vents are provided. If such vacuum is formed, air may be forced back into the guiding introducer system by the reintroduction of a catheter 50 into the lumen of the inner guiding introducer. Such air could cause significant problems in the patient, including the possibility of a stroke, heart attack or other such problems common with air in the heart. The addition of vents near the distal tip of the inner 60 and outer 70 guiding introducer prevents the formation of such vacuum by permitting fluid, presumably blood, to be drawn into the lumen of the inner 60 and outer 70 guiding introducer as the catheter is being removed from the inner guiding introducer, 60 thus preventing the creation of a vacuum which could cause air to enter the guiding introducer system.

The inner 60 and outer 70 guiding introducers may be made of any material suitable for use in humans which has a memory or permits distortion from, and substantial return to, the desired three dimensional shape. For the purpose of illustration and not limitation, the internal diameter of the inner 60 and outer 70 guiding introducer may vary from about 6 to about 12 "French" respectively (1 French equals ⅓ of a millimeter). Such inner 60 and outer 70 guiding introducers can also accept dilators and appropriate guidewires. Obviously, if larger or smaller dilators or catheters are used in conjunction with the guiding introducer system of the instant invention, modifications in size or shape can be made to the inner and outer guiding introducer.

Variations in size and shape of the inner 60 and outer 70 guiding introducer are also intended to encompass pediatric uses, although the preferred uses are for adult human hearts. It is well recognized that pediatric uses may require reductions in size of the various sections of the inner 60 and outer 70 guiding introducer, in particular the first section 62, 72, but without any significant modification to the shape or curve of the inner 60 and outer 70 guiding introducer.

In addition, variations in size or shape of the inner 60 and outer 70 guiding introducers are also intended to encompass the specialized situations that sometimes occur in patients with enlarged or rotated hearts.

By extending the distal tip of the inner guiding introducer 60 away from the distal tip of the outer guiding introducer 70 and by rotating the inner guiding introducer 60 with respect to the outer guiding introducer, 70 a variety of shapes of the overall guiding introducer system are formed which are helpful in directing the mapping and/or ablation catheter 50 toward the site within the left ventricle of interest. These shapes permit ablation procedures within the left ventricle to be performed, for example, around the mitral valve annulus in various positions such as anterior 24 to anterolateral to lateral 16 to posterolateral 20 to posteroseptal to septal 22. See FIG. 1A. The various locations can be treated by extending the inner guiding introducer 60 away from the outer guiding introducer 70 which forms a different overall shape and/or by rotating the inner guiding introducer 60 with respect to the outer guiding introducer 70. In addition, by manipulation of the inner guiding introducer 60 within the outer guiding introducer 70, additional procedures can be performed within the left ventricle. Being able to extend the inner guiding introducer 60 within the outer guiding introducer 70 and to rotate the inner guiding introducer 60 within the outer guiding introducer 70 permits a wide variety of overall shapes, which is particularly useful to medical practitioners. The medical practitioner is able to determine the relative location of the inner 60 and outer 70 guiding introducers because of the tip markers located near the distal tip of both the inner 60 and outer 70 guiding introducers.

The relative diameter of the outer guiding introducer 70 in relation to that of the inner guiding introducer 60 should be sufficient to permit the inner guiding introducer 60 to be torqued or rotated within the outer guiding introducer 70 without undue restriction on such movement. Preferably, the difference in size between the inner 60 and outer 70 guiding introducer should be at least about 3 French. For example in one preferred embodiment, the outer guiding introducer is 11 French in size and the inner guiding introducer is 8 French. By this difference in diameter, there is approximately 1 French unit of space available between the outer surface of the inner guiding introducer 60 and the inner surface of the outer guiding introducer 70. Preferably, this space between the inner 60 and outer 70 guiding introducer is filled with a biocompatible solution, such as a saline solution, preferably a heparinized saline solution. This saline solution also provides lubricity to the inner 60 and outer 70 guiding introducers, allowing more accurate torquing of the inner guiding introducer 60 within the outer guiding introducer 70. In addition, it is preferable that the structure of both the inner 60 and the outer 70 guiding introducer have a high torsional constant to allow for the full utilization of the various shapes available by rotation and extension of the inner 60 in relation to the outer 70 guiding introducer. To permit this high torsional constant, in one preferred embodiment the inner guiding introducer 60 is braided to provide further strength and structural stability.

In operation, a modified Seldinger technique is normally used for the insertion of the catheter 50 into the femoral artery. The appropriate vessel is accessed by needle puncture. A soft flexible tip of an appropriately sized guidewire is then inserted through and a short distance beyond the needle into the vessel. Firmly holding the guidewire in place, the needle is removed. The guidewire is then advanced through the artery up to the aorta, across the aortic valve into the left ventricle. With the guidewire in place, a dilator is then placed over the guidewire with the guiding introducer system placed over the dilator. The dilator and guiding introducer system generally form an assembly to be advanced together along the guidewire into the left ventricle. After insertion of the assembly, the guidewire and dilator are then withdrawn. The catheter 50 to be used for analysis and/or treatment of the anomalous conduction pathways is advanced through the lumen of the inner guiding introducer 60 and is placed at an appropriate location near the mitral valve annulus.

By extending and withdrawing the inner guiding introducer 60 in relation to the outer guiding introducer 70 and by rotating the inner guiding introducer 60 within the outer guiding introducer, 70 great variances in the overall shape and location of the guiding introducer system can be achieved.

By movement of the inner guiding introducer 60 within the outer guiding introducer 70 in conjunction with fluoroscopic viewing, the distal portion of the outer guiding introducer 70 can be manipulated to direct the distal end of a catheter 50 placed within the lumen of the inner guiding introducer 60 to a specific internal surface within the left ventricle. In addition, by providing sufficient rigidity, the distal end of the inner guiding introducer 60 can be maintained in that fixed location or surface position of the endocardial structure to permit the appropriate procedures to be performed. If sensing procedures are involved, the guiding introducer system is maneuvered to the desired location. At that point, the electrical activity of the heart peculiar to that location can be precisely determined by use of an electrophysiology catheter placed within the guiding introducer system. Further, as the guiding introducer system permits precise location of catheters, an ablation catheter may be placed at a precise location for destruction of the cardiac tissue by the use of energy, for example, radio frequency, thermal, laser or direct current (high energy direct, low energy direct and fulgutronization procedures.) Preferably, radio frequency energy is utilized for the ablation procedure.

The precise placement of the ablation catheter electrode is important as there will be no dilution of the energy delivered due to unfocused energy being dissipated over the cardiac chamber and lost in the circulating blood by a constantly moving electrode of the ablation catheter. This system permits a significantly reduced amount of energy to be applied while still achieving efficient ablation. Further, time used to perform the procedure is significantly reduced over procedures where no guiding introducer is used. This reduction in time also reduces the amount of fluoroscopy that is necessary for the procedure.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A process for ablating and mapping accessory pathways around the mitral valve of the left ventricle of the heart comprising
   (a) introducing into the left ventricle a guiding introducer system, comprising a precurved inner and a precurved outer guiding introducer, wherein each guiding introducer contains a lumen running lengthwise therethrough, a proximal and a distal end;
   (b) introducing the inner guiding introducer into the lumen of the outer guiding introducer;
   (c) introducing into the lumen of the inner guiding introducer an ablating and mapping catheter containing a proximal and a distal end, wherein said catheter has one or more electrodes located near the distal end of the catheter,
   (d) guiding the catheter to a selected location about the mitral valve of the heart on the ventricular side by use of the guiding introducer system, and
   (e) mapping and ablating the selected location about the mitral valve of the heart by use of the electrodes of the catheter.

2. The process of claim 1 wherein the ablating utilizes one of the following sources of energy: direct current, including high energy direct current, low energy direct current or fulgutronization procedures, microwave, ultrasound, laser procedures, and radio frequency.

3. The process of claim 2 wherein the ablating is performed utilizing radio frequency energy.

4. The process of claim 1 wherein the inner guiding introducer is comprised of a first and second sections.

5. The process of claim 4 wherein the first section of the inner guiding introducer is an elongated, hollow, generally straight section of sufficient length for introduction into the patient and for manipulation from the point of insertion through to a desired location within the heart.

6. The process of claim 4 wherein the second section of the inner guiding introducer is a generally curved section with an overall radius of about 0.5 in. to about 1.5 in., and an overall arc from about 45 to about 135 degrees.

7. The process of claim 4 wherein the second section of the inner guiding introducer is a generally curved section with a radius from about 0.8 in. to about 1.2 in. and an arc from about 60 to about 120 degrees.

8. The process of claim 4 wherein the second section of the inner guiding introducer is a curved section with an overall arc, comprising a curved portion, wherein the overall arc of the curved section is from about 45 to about 135 degrees.

9. The process of claim 8 wherein the inner guiding introducer also includes a straight portion incorporated with the curved portion.

10. The process of claim 1 wherein the outer guiding introducer is comprised of first and second sections.

11. The process of claim 10 wherein the first section of the outer guiding introducer is an elongated, hollow, generally straight section of sufficient length for introduction into the patient and for manipulation from the point of insertion through to a desired location within the heart.

12. The process of claim 10 wherein the second section of the outer guiding introducer is a generally curved section with an overall radius of about 1.0 in. to about 2.0 in. and an overall arc from about 135 to about 225 degrees.

13. The process of claim 10 wherein the second section of the outer guiding introducer is a curved section with a radius of about 1.3 in. to about 1.7 in. and an arc from about 160 to about 200 degrees.

14. The process of claim 10 wherein the second section of the outer guiding introducer is a curved section with an overall arc, comprising a curved portion, wherein the overall arc is from about 135 to about 225 degrees.

15. The process of claim 14 wherein the outer guiding introducer also includes a straight portion.

16. A guiding introducer system for use with an ablating catheter for ablating and mapping accessory pathways around the mitral valve of the left ventricle of the heart comprising a precurved inner and a precurved other guiding introducer, wherein each guiding introducer contains a lumen running lengthwise therethrough, a proximal and a distal end.

17. The guiding introducer section of claim 16 wherein the inner guiding introducer comprises first and second sections.

18. The guiding introducer of claim 17 wherein the first section of the inner guiding introducer is an elongated, hollow, generally straight section of sufficient length for introduction into the patient and for manipulation from the point of insertion through to a desired location within the heart.

19. The guiding introducer system of claim 17 wherein the second section is a generally curved section with an overall radius of about 0.5 in. to about 1.5 in., and an overall arc from about 45 to about 135 degrees.

20. The guiding introducer system of claim 17 wherein the second section comprises a generally curved section with an overall radius of about 0.8 in. to about 1.2 in., and an overall arc from about 60 to about 120 degrees.

21. The guiding introducer of claim 17 wherein the second section is a curved section with an overall arc, comprising an individual curved portion, wherein the overall arc is from about 45 to about 135 degrees.

22. The guiding introducer of claim 21 wherein a straight portion is included with the curved portion.

23. The guiding introducer system of claim 16 wherein the outer guiding introducer is comprised of a first and second sections.

24. The guiding introducer system of claim 23 wherein the first section of the outer guiding introducer is an elongated, hollow, generally straight section of sufficient length for introduction into the patient and for manipulation from the point of insertion through to a desired location within the heart.

25. The guiding introducer system of claim 23 wherein the second section of the outer guiding introducer is a generally curved section with an overall radius of about 1.0 in. to about 2.0 in. and an overall arc from about 135 to about 225 degrees.

26. The guiding introducer system of claim 23 wherein the second section of the outer guiding introducer is a generally curved section with a radius of about 1.3 in. to about 1.7 in. and an overall arc from about 160 to about 200 degrees.

27. The guiding introducer system of claim 23 wherein the second section of the guiding introducer comprises a generally curved section with an overall arc, comprising an individual curved portion, wherein the overall arc is from about 135 to about 225 degrees.

28. The guiding introducer system of claim 27 wherein a straight portion is combined with the curved portion.

* * * * *